United States Patent
Hermansson et al.

(10) Patent No.: US 9,351,812 B2
(45) Date of Patent: May 31, 2016

(54) CALCIUM ALUMINATE BASED PASTE FOR STABILIZING DENTAL IMPLANTS AND RESTORING TISSUE ATTACHMENT AFTER SURGERY AND METHODS THEREFOR

(71) Applicant: DOXA AB, Uppsala (SE)

(72) Inventors: Leif Hermansson, Mölle (SE); Jesper Lööf, Bälinge (SE); Per-Olof Glantz, Malmö (SE); Emil Abrahamsson, Storvreta (SE)

(73) Assignee: DOXA AB, Uppsala (SE)

( * ) Notice: Subject to any disclaimer, the term of this patent is extended or adjusted under 35 U.S.C. 154(b) by 106 days.

(21) Appl. No.: 14/171,038

(22) Filed: Feb. 3, 2014

(65) Prior Publication Data

US 2014/0147811 A1     May 29, 2014

Related U.S. Application Data

(62) Division of application No. 13/499,359, filed as application No. PCT/SE2009/051097 on Oct. 2, 2009, now abandoned.

(51) Int. Cl.

| | |
|---|---|
| *A61C 5/00* | (2006.01) |
| *A61C 8/02* | (2006.01) |
| *A61K 6/06* | (2006.01) |
| *A61L 27/30* | (2006.01) |
| *C04B 28/06* | (2006.01) |
| *C04B 41/00* | (2006.01) |
| *C04B 41/50* | (2006.01) |
| *C04B 41/85* | (2006.01) |
| *A61C 8/00* | (2006.01) |
| *C04B 111/00* | (2006.01) |

(52) U.S. Cl.
CPC .............. *A61C 8/0006* (2013.01); *A61C 8/0013* (2013.01); *A61K 6/0612* (2013.01); *A61K 6/0637* (2013.01); *A61L 27/30* (2013.01); *C04B 28/06* (2013.01); *C04B 41/009* (2013.01); *C04B 41/508* (2013.01); *C04B 41/85* (2013.01); *C04B 2111/00215* (2013.01); *C04B 2111/00836* (2013.01)

(58) Field of Classification Search
CPC ..... A61K 6/02; A61K 6/0008; A61K 6/0017; A61K 6/0038; A61K 6/0073; A61K 6/0637; A61C 8/00; A61C 8/0013; A61C 5/02
USPC ........... 433/172–176, 201.1, 215, 216, 217.1, 433/228.1; 423/600, 119; 106/35, 692, 695, 106/470; 427/2.26; 623/23.51, 23.56; 523/115–118
See application file for complete search history.

(56) References Cited

U.S. PATENT DOCUMENTS

| | | | |
|---|---|---|---|
| 6,220,861 B1 | 4/2001 | Kwon et al. | |
| 6,273,717 B1 | 8/2001 | Hahn et al. | |
| 6,758,844 B2 | 7/2004 | Neuberger | |
| 7,172,594 B2 | 2/2007 | Biscup | |
| 2003/0220414 A1* | 11/2003 | Axen et al. | 523/116 |
| 2004/0117030 A1* | 6/2004 | Axen et al. | 623/23.51 |
| 2007/0020582 A1 | 1/2007 | Neumeyer | |

FOREIGN PATENT DOCUMENTS

| | | |
|---|---|---|
| EP | 1980276 A1 | 10/2008 |
| WO | 03074097 A1 | 9/2003 |
| WO | 2004028577 A1 | 4/2004 |
| WO | 2005039508 A1 | 5/2005 |
| WO | 2005053764 A1 | 6/2005 |
| WO | 2008105738 A1 | 9/2008 |
| WO | 2009025599 A1 | 2/2009 |

OTHER PUBLICATIONS

International Search Report of the International Searching Authority for International Application No. PCT/SE2009/051097; International Filing Date: Oct. 2, 2009; Date of mailing: Mar. 3, 2010; 4 Pages.

Written Opinion of the International Searching Authority for International Application No. PCT/SE2009/051097; International Filing Date: Oct. 2, 2009; Date of mailing: Mar. 3, 2010; 6 Pages.

* cited by examiner

*Primary Examiner* — Yogesh Patel
(74) *Attorney, Agent, or Firm* — Cantor Colburn LLP

(57) ABSTRACT

The present invention relates to a calcium aluminate based paste forming a chemically bonded biomaterial on hydration thereof for in vivo anchoring of new implants, or stabilizing of existing implants in situ to an adjacent bone tissue, which paste provides a controlled pH value and temperature as well as initial hardening time. By virtue of the pH value and temperature the paste exhibits antibacterial and/or bacteriostatic properties. The present invention also relates to a method of preparing implants to be implanted wherein the implant is coated with the paste, a method of implanting a coated implant, as well as methods of preventing and treating implant related conditions, such as periimplantitis, and kit for preparing the paste. The invention is especially intended for re-stabilization of dental implants, and implantation into low quality bone tissue.

8 Claims, No Drawings

CALCIUM ALUMINATE BASED PASTE FOR STABILIZING DENTAL IMPLANTS AND RESTORING TISSUE ATTACHMENT AFTER SURGERY AND METHODS THEREFOR

CROSS-REFERENCE TO RELATED APPLICATIONS

This Application is a Divisional of U.S. Ser. No. 13/499,359 filed Mar. 30, 2012, which is a US National Stage of International Patent Application PCT/SE2009/051097 filed Oct. 2, 2009, both of which are incorporated by reference in their entirety.

TECHNICAL FIELD

The present invention relates to a calcium aluminate based paste forming a chemically bonded biomaterial on hydration thereof for in vivo anchoring of new implants, or stabilizing of existing implants in situ to an adjacent biologic tissue, which paste provides a controlled pH value and temperature as well as initial hardening time. By virtue of the pH value and temperature the paste exhibits antibacterial and/or bacteriostatic properties. The present invention also relates to a method of preparing implants to be implanted wherein the implant is coated with the paste, a method of implanting a coated implant, as well as methods of preventing and treating implant related conditions, such as periimplantitis, and a kit for preparing the paste. The invention is especially intended for stabilization of dental implants, in low quality bone tissue, and to restore tissue attachment of dental implants after surgery.

RELATED ART

In implants that are to interact with the human body, it is advantageous to use implant materials that due to their biocompatibility will provide an optimal fixation or anchoring of the implant to the surrounding biological tissue, e.g. bone. Even small gaps between the implant and surrounding tissue may lead to small movements, such as micro-motions, of the implant in relation to the tissue, which will increase the risk of implant loosening, e.g. due to formation of zones of fibrous tissue at the implant-tissue interface. Porosity or cavities in the tissue surface (vacuoles) also reduce the implant fixation. In order to allow for early loading of an implant and to reduce the risk for long term loosening, high quality early fixation of the implant the surrounding tissue is important. WO2005/053764 discloses dental and orthopaedic implants aiming at fulfilling the above requirements. More particularly, the coated implant disclosed therein comprises an implant having a pre-treated surface on said pre-treated surface one or more layers of a material with a phase having the capacity following wetting with a liquid to form a chemically bonded ceramic material. The material of said one or more layers is substantially non-hydrated prior to said in vivo-anchoring, and said one or more layers have the capability to chemically and/or mechanically bind to said implant and optionally to a paste of a powdered material with a calcium-based binder phase having the capacity following wetting with a liquid reacting with it to form a chemically bonded ceramic material.

For simplicity, conventional abbreviations for the calcium aluminate phases will be used herein. Accordingly, e.g. the term "$C_3A$" is used to denote the calcium aluminate phase $3CaO.Al_2O_3$, and the term "$C_3S$" is used to denote the calcium silicate phase $3CaO.SiO_2$.

WO2004/028577 discloses an injectable biocompatible cement composition formed from a hydraulic powder raw material, predominantly comprising the following calcium aluminate phases; $CA_2$, $CA$, $C_{12}A_7$, and $C_3A$ and an aqueous hydration liquid which in a preferred embodiment may contain LiCl as an accelerator. The composition may additionally comprise a non-hydraulic filler. Preferably the grain size of the powder/particle raw material used is predominately less than 3 μm. The injectable cement composition can be used for e.g. treatment of cancer by means of the heat generated in vivo upon curing of the cement composition disclosed therein.

It has recently been found that existing ceramic materials, such as that disclosed in WO2005/053764 may not be suitable for use in low quality bone tissue in that it tends to provide inferior fixation to such low quality tissue. Accordingly, it would be desirable to provide a material providing improved fixation of an implant to low quality bone tissue.

The inventors have found that a paste formed from a powder comprising a powdered cement and optionally, inert filler particles, which cement is based on calcium aluminate and a hydration liquid containing LiCl, wherein the calcium aluminate consists of the phases CA and/or $C_{12}A_7$, and optionally $C_3A$, and wherein the mean particle size of the powdered cement is within the interval of 2-7 μm, and the powder to liquid ratio is 2.0:1 to 5.0:1, will provide the desired fixation.

The powdered cement may optionally also contain $C_3S$ having a mean particle size within the above range.

The combined amounts of any $C_3A$ and $C_3S$ present should not exceed 10% by weight of the cement.

SUMMARY OF INVENTION

The invention is based on the finding that the selected phases of calcium aluminate (i.e. CA, $C_{12}A_7$, and $C_3A$), optionally together with the calcium silicate phase $C_3S$ in the specified particle range will provide for a system with well-defined properties in terms of pH and heat generated on curing thereof. The curing reaction within the inventive paste is believed to be essentially homogeneous. Also, since the selected phases are relatively reactive, hardening will be rapid, and initial fixation will be accomplished in terms of a few minutes. In order to safeguard the desired homogenous reaction characteristics within the paste, and the desired well-defined properties in terms of pH and heat generated on curing thereof, the inventive, highly reactive paste should be used in small volumes. Preferably the total amount of paste used on an implant should not exceed 0.8, and should more preferably not exceed 0.5 cm$^3$.

When used in such small amounts, the material is believed to be tolerable to surrounding tissue, since the pH increase and temperature increase will only be transitional and moreover closely predictable.

The pH increase and moderately elevated temperature generated upon curing is also believed to produce an antibacterial, bacteriostatic and/or anti-inflammatory effect in the surrounding tissue. By the same token the inventive paste is also believed to be beneficial in preventing and treating implant related medical conditions, such as periimplantitis.

In the prior art the problem periimplantitis and other implant related illnesses have been dealt with using anti-inflammatory particles (EP 1 980 276 A1), electrostimulation (U.S. Pat. No. 7,172,594 B2), sonic or ultra sonic treatments (U.S. Pat. No. 6,273,717 B2), laser radiation and handpiece (U.S. Pat. No. 6,758,844 B2), implant band (U.S. Pat. No. 6,220,861 B1) or a medical delivery device in general.

The ratio of C to A in the phases of the calcium aluminate in the inventive paste must not be lower than unity. Accordingly, the calcium aluminate phases used in the invention are selected from CA, $C_{12}A_7$ and $C_3A$. For example, the phase $CA_2$ used in WO2004/028577 is too slowly reacting and should not be present. Inclusion thereof would delay the initial fixation and prolong tissue exposure to the conditions of elevated temperature and pH value.

When the CA phase is synthesized, a minor amount of $CA_2$ is normally also formed. The amount of $CA_2$ should be restricted to <6% by weight of the CA, preferably <4%.

The present application deals specifically with implantation in low quality bone tissue, and also with cases where there is a need of re-stabilization of an existing implant in a subject.

The inventive paste can be applied in situ to the surface of an existing implant in a patient, such as by means of injection. Such application of the paste can be used in re-stabilization of an implant in situ. Accordingly, the present invention also provides for re-stabilization of implants after damage of surrounding tissue.

The inventive paste can also be applied to a surface of an implant to be implanted, by means of e.g. dipping the implant in the paste before inserting the implant. Alternatively, the paste can be filled into a predrilled hole in the bone before inserting the implant into said hole. Such application of the paste can be used in implantation of an implant into low quality bone tissue, and is also suitable for preventing implant related medical conditions.

The present invention thus provides for a simplified application of the ceramic material to a surface of an implant, as compared to e.g. WO2005/053764.

By virtue of the inventive material being in the form of a paste, the desired improved bone gap filling properties are also accomplished.

Accordingly, in a first aspect the present invention relates to a calcium aluminate based paste forming a chemically bonded biomaterial on hydration thereof, which paste is obtainable by mixing a powder comprising a powdered cement and optionally, inert filler particles, which cement is based on calcium aluminate, and an aqueous hydration liquid containing LiCl, wherein the calcium aluminate consists of particles of the phases CA and/or $C_{12}A_7$, and optionally $C_3A$, wherein the cement may additionally comprise the calcium silicate phase $C_3S$, and wherein the combined amounts of any $C_3A$ and $C_3S$ present do not exceed 10% by weight of the cement, and wherein the cement particles exhibit a mean particle size within the interval of 2-7 μm, and the powder to liquid ratio is within the range of 2.0:1 to 5.0:1.

In another aspect the invention relates to a method of preparing an implant suitable for implantation into low quality bone tissue comprising the following steps: providing a powder comprising a powdered cement and optionally, inert filler particles, which cement is based on calcium aluminate; providing an aqueous hydration liquid containing LiCl; mixing the powdered cement and hydration liquid so as to form a paste; wherein the paste thus formed is applied to a surface of an implant, which surface is to be in contact with bone tissue; wherein the calcium aluminate consists of particles of the phases CA and/or $C_{12}A_7$, and optionally $C_3A$, wherein the cement may additionally comprise the calcium silicate phase $C_3S$, and wherein the combined amounts of any $C_3A$ and $C_3S$ present do not exceed 10% by weight of the cement, and wherein the cement particles exhibit a mean particle size within the interval of 2-7 and the powder to liquid ratio is within the range of 2.0:1 to 5.0:1.

In a further aspect the invention relates to the use of the above method for preventing an implant related disease, such as periimplantitis, in a subject in the need of a dental implant.

In yet an aspect the invention relates to a method of implanting an implant, which method is suitable for implantation into low quality bone tissue in a subject comprising the following steps: providing a powder comprising a powdered cement and optionally, inert filler particles, which cement is based on calcium aluminate; providing an aqueous hydration liquid containing LiCl; mixing the powdered cement and hydration liquid so as to form a paste; wherein the thus formed paste is applied to a surface of an implant, which surface is to be in contact with bone tissue, and/or wherein the thus formed paste is filled into a pre-drilled hole in the bone tissue into which hole the implant is to be inserted; and implanting the coated implant into the bone tissue; wherein the calcium aluminate consists of particles of the phases CA and/or $C_{12}A_7$, and optionally $C_3A$, wherein the cement may additionally comprise the calcium silicate phase $C_3S$, and wherein the combined amounts of any $C_3A$ and $C_3S$ present do not exceed 10% by weight of the cement, and wherein the cement particles exhibit a mean particle size within the interval of 2-7 μm, and the powder to liquid ratio is within the range of 2.0:1 to 5.0:1.

In another aspect the present invention relates to a method of preventing an implant-related illness, such as periimplantitis, in a subject in the need of an implant, wherein the above method of implantation is used.

In a further aspect the invention relates to a method of in situ re-stabilizing an existing implant in bone tissue in a subject, which method is suitable for re-stabilizing an implant in low quality bone tissue, comprising the following steps: providing a powder comprising a powdered cement and optionally, inert filler particles, which cement is based on calcium aluminate; providing an aqueous hydration liquid containing LiCl; mixing the powdered cement and hydration liquid so as to form a paste; and, applying the paste to a surface of an existing implant in need of re-stabilization in bone tissue in a subject, which surface is to be in contact with bone tissue; wherein the calcium aluminate consists of particles of the phases CA and/or $C_{12}A_7$, and optionally $C_3A$, wherein the cement may additionally comprise the calcium silicate phase $C_3S$, and wherein the combined amounts of any $C_3A$ and $C_3S$ present do not exceed 10% by weight of the cement, and wherein the cement particles exhibit a mean particle size within the interval of 2-7 μm, and the powder to liquid ratio is within the range of 2.0:1 to 5.0:1.

In a further aspect the present invention relates to a method for in situ treatment of an implant-related illness, such as periimplantitis, in a subject wherein the implant is located in said subject.

In yet a further aspect the invention relates to a kit for use in preparing the paste, comprising a powder comprising a powdered cement and optionally, inert filler particles, which cement is based on calcium aluminate, wherein the calcium aluminate consists of particles of the phases CA and/or $C_{12}A_7$, and optionally $C_3A$, wherein the cement may additionally comprise the calcium silicate phase $C_3S$, and wherein the combined amounts of any $C_3A$ and $C_3S$ present do not exceed 10% by weight of the cement, and wherein the cement particles exhibit a mean particle size within the interval of 2-7 μm; and an aqueous hydration liquid containing LiCl, in a powder to liquid ratio within the range of 2.0:1 to 5.0:1, in amounts effective to provide no more than 0.8 cm³ of paste, and more preferably no more than 0.5 cm³ of paste.

Further aspects and preferred embodiments will become apparent from the following detailed description and appended claims.

As used herein, the expressions "calcium aluminate based paste", and "powdered cement based on calcium aluminate", respectively, are used to denote a paste, and a ceramic powder from which the paste is formed, respectively, the ceramic binder (i.e. the powdered cement) of which paste and powder, respectively, is based on calcium aluminate of the above selected phases, optionally together with $C_3S$.

Preferably the ceramic binder (i.e. the powdered cement) consists of CA and/or $C_{12}A_7$, and optionally $C_3A$ and/or $C_3S$, except for any $CA_2$ that may be present in the powder as an impurity resulting from the CA synthesis.

DETAILED DESCRIPTION OF THE INVENTION

The present invention i.a. aims at providing a system based on a chemically bonded ceramic material (CBC material), for in vivo for improved anchoring of an implant to bone tissue, especially to low quality bone tissue, and also for re-anchoring of implants to a biological tissue due to e.g. periimplantitis.

The inventive paste can be used for anchoring in bone tissue an implant to be implanted into said tissue. The paste may be applied to a surface of the implant, which surface is to be in contact with the bone tissue. The application can be carried out by e.g. dipping the surface into the paste. Thereafter, the thus coated implant is implanted into the bone tissue. Typically, the implant is inserted into a matching pre-drilled hole in the bone tissue. Accordingly, the paste may alternatively be filled into said hole, such as by injection, before inserting the un-coated implant into said hole. It is of course also possible to use a combination thereof, i.e. to apply some of the paste to the surface of the implant and to fill some of the paste into the hole.

In a preferred embodiment the surface of the implant to which surface the paste is to be applied is treated with an aqueous solution of $C_3S$, CaO and/or $C_3A$ before applying the paste to said surface. By doing so, the surface will be cleaned, and the treatment will also serve to transitionally boost the initial pH-value. Thereby, the desired anti-inflammatory and antibacterial effects, as well as the anchoring to the surrounding bone tissue will be enhanced. Any surplus aqueous solution is preferably removed from the surface, before applying the paste to said surface. The pre-drilled hole also be treated with an aqueous solution of $C_3S$, CaO and/or $C_3A$ before filling the paste into said hole. These very active Ca-phases are believed to be able to destroy any undesired biofilms on the implant surface.

Accordingly, by virtue of the anti-inflammatory and antibacterial properties of the inventive paste upon hydration thereof, an implant to be implanted, which has been coated with the inventive paste, can be used for preventing an implant related illness, such as periimplantitis, in a subject in the need of the implant.

The inventive paste can also be used for re-stabilization, or re-anchoring in situ an existing implant in bone tissue in a subject. In this case the paste is applied to a surface of the implant to be re-stabilized or re-anchored, which surface is to be in contact with the surrounding bone tissue. The application of the paste to the surface can be carried out e.g. by injection.

In a preferred embodiment of the method the surface of the implant to which surface the paste is to be applied is treated with an aqueous solution of $C_3S$, CaO and/or $C_3A$ before applying the paste to said surface. By doing so, the surface will be cleaned, and the treatment will also serve to transitionally boost the initial pH-value. Thereby, the desired anti-inflammatory and antibacterial effects, as well as the anchoring to the surrounding bone tissue will be enhanced. Any surplus aqueous solution is preferably removed, e.g. by wiping with a tissue, before applying the paste to said surface.

Accordingly, by virtue of the anti-inflammatory and antibacterial properties of the inventive paste upon hydration thereof, this method can be used for the in situ treatment of an implant-related illness, such as periimplantitis, in a subject in need of re-stabilization, or re-anchoring of an existing implant, especially a dental implant.

The use of a paste of the present invention allows for enhanced contact of the ceramic material with the bone tissue, and also of the ceramic material with an implant, as compared to e.g. a powder coating. Thereby, a more fully contact will be established. The inventive paste will effectively fill voids surrounding the in situ implant, such as the gap between the implant and the biological tissue, and any vacuoles or cavities in the surface of the bone tissue. This property of the inventive paste will make it well suited for use with bone tissue of poor or low quality.

The use of the paste of the invention also provides for a reduced time required for anchoring and stabilization of the implant, i.e. an early anchoring and stabilization.

The mechanisms underlying the anchoring of the CBC-paste to the implant, as well as to the bone tissue, occur by precipitation of nanosize hydrates of the system CaO—$Al_2O_3$—$P_2O_5$—$CO_2$—$H_2O$, i.e. the phases formed of calcium aluminate in water containing hydro-phosphates and hydrocarbonate.

The inventive paste will produce a controlled pH increase during initial curing, and a controlled temperature increase during the initial hydration. The pH and temperature changes will also be controlled in terms of time (i.e. onset and duration).

Preferably, the pH interval during hydration is controlled to be within the interval of 8.5-12.5, the temperature is controlled to be within the interval of 37-60° C., and the hydration time is controlled to be within the range of 5-60 minutes. The pH, temperature and hydration time ranges are obtained by using the claimed paste. For a hydration time of >10 minutes, the presence of a retarder will be required. The retarder is also being referred to herein as a $Ca^{2+}$ scavenging chelating agent.

The retarder may be selected from any retarders conventionally used in CBC biomaterials, such as citric acid, citrates, tartrates, and EDTA in an amount from 0.2-2% by weight based on the total weight of the hydration liquid. The retarder may be added in dry form to the powder, or may be dissolved directly in the aqueous hydration liquid. Preferably, the liquid comprises 0.4-1.5 wt-% of a $Ca^{2+}$ scavenging chelating agent, and preferably the agent is a tartrate.

By virtue of the above controlled pH and temperature increase, the paste will produce an anti-inflammatory and antibacterial effect during setting and curing.

The volume of the paste to be inserted/injected and/or applied to a surface of the implant does preferably not exceed 0.8 $cm^3$, and more preferably does not exceed 0.5 $cm^3$. The paste exhibits exothermal reacting properties and, according to the invention, these are controlled by the CA phases selected, the original particle size of the powder, the amount of liquid, and also by the paste volume selected.

In a preferred embodiment, the powdered material to be used in the paste has a mean particle size of 3 to 4 µm. This will further improve the time for establishing the required anchoring and stabilization of the implant. All the particles will be hydrated in a short time with the desired properties (pH, temperature and reaction time) according to the invention.

According to the invention the pH upon initial setting and curing is preferably controlled so as to be within the interval of 12.5-8.5 for a duration of less than 10 minutes following implantation, and more preferably within the interval of 11-9 during the first 20 minutes after injection/insertion.

According to the invention the elevated temperature during hydration/curing is preferably controlled so as to be within the interval of 40-60° C. for a duration of less than 20 minutes following implantation.

The implant may be made of a ceramic, metallic or polymeric material, and preferably a material chosen from the group consisting of titanium, stainless steels, alumina, zirconia and medical grade plastics.

The hydration liquid preferably comprises 10-200 mM of LiCl, and deionised water to 100%.

The powder to liquid ratio (2.0:1-5.0:1) varies mainly due to the presence of filler particles in the powder, and more specifically the amount and density thereof, and should preferably be selected so that the water to cement ratio by weight is within the interval close to complete dissolution of the calcium aluminate phases, which is approximately in the interval of 0.40 to 0.46.

The density of the filler particles may typically vary from about 2.5 to about 6 g/cm$^3$.

The amount of calcium aluminate phases in the powder also varies mainly depending on the density of the filler particles used and the amount thereof, but will typically be within the range of 30% to 70% by weight of the powder.

Suitable inert filler materials are inert oxides or glasses, preferably oxides of elements of density above 5 g/cm$^3$ (such as Zr, Zn etc). Glasses or glass-ceramics or hydrated calcium aluminate (all containing elements of density above 5 g/cm$^3$) could also be used.

The CA phases of the calcium aluminate powder used in the present invention can be in crystalline or amorphous state.

The calcium aluminate phases used in the inventive paste will be based on either of CA and $C_{12}A_7$, or a combination thereof. Both of these phases, alone or in combination, will provide a paste having curing and setting properties which can be closely regulated. $C_3A$ and/or $C_3S$, being highly reactive, may be included in minor amounts if a higher temperature upon hydration is desired. The total amount of any $C_3A$ and/or $C_3S$ present should not exceed 10% by weight of the cement powder.

To the calcium aluminate based paste an organic constituent may be added, such as tartaric acid, poly acrylic acid in order to obtain desired properties in terms of rheological properties, a low w/c ratio, or to work as a complementary binding system. This phase also endows the system with a more visco-elastic behaviour with an increased strength of the end product The healing or growing process of the bone is favoured by an early fixation (less micromotion leading to less fibrous tissue) and by the supply of calcium and phosphate and carbonate from the cement-body liquid system. The dissolution-precipitation of the calcium aluminate based system process is able to fill large gaps (mm size).

The paste of the invention should be sterile. The powder of the invention should be kept dry and sterile. Accordingly, the powder should e.g. be sterilized and transferred to a suitable sterile container, which thereafter is sealed under sterile conditions, and stored dry. Similarly, the liquid should also be sterilized before mixing with the powder.

In order for the invention to be more fully understood the following examples are provided.

Description of Raw Materials and Preparation

Example 1

Preparation of the Powder

The calcium aluminate used for this material is synthesised using high purity $Al_2O_3$ and either of CaO and $CaCO_3$. The correct amount of the raw materials are weighed in to a suitable container (i.e. 1:1 molar ratio for CA, and 12:7 for $C_{12}A_7$, and 3:1 for $C_3A$). The powders are intimately mixed by tumbling in excess isopropanol or tumbled dry using a dry powder mixer. If mixing in isopropanol is performed the next step will be removing the isopropanol, such as by evaporation of the solvent using an evaporator combining vacuum and heat and finally a heating oven. Thereafter high purity $Al_2O_3$ crucibles are filled with the different calcium aluminate phases used, and the powders are heat treated at 1425° C. for 5 h in the case of CA, at 1360° C. for 5 h for $C_{12}A_7$, and at 1400° C. in the case of $C_3A$. After the heat treatment the powder materials are crushed using a high energy crusher. In this example a roller crusher with alumina rollers was used. After crushing the calcium aluminate phase is milled to the specified particle size distribution with a $d(99)_r$ of <10 µm. The final powder formulation was obtained as follows: All powder components were weighed in with high accuracy according to the composition in table 1.

TABLE 1

| Composition of the final powder formulation. | |
| --- | --- |
| Raw material | Wt % |
| Calcium aluminate-CA phase | 37.50 |
| Calcium aluminate-$C_{12}A_7$ phase | 5.00 |
| Calcium aluminate-$C_3A$ phase | 5.00 |
| $ZrO_2$-monoclinic | 52.50 |

The components are weighed into a glass beaker, and the beaker is thereafter placed in a dry mixer and the components mixed at medium speed for 3 hours. The next step after mixing is sieving through a 125 µm sieve in order to homogenise the powder and remove large agglomerates. After sieving the powder is transferred to a suitable container, sealed, sterilised and stored dry. The powder is now ready for use.

Example 2

Preparation of the Liquid

The LiCl is first dried at 150° C. for at least 2 hours in order to remove physically bound water. The LiCl was weighed into a PE bottle so that the final composition after addition of the water will be 20 mM of LiCl. After the water has been added the bottle is shaken until all the salts have dissolved. The liquid is sterilised. Thereafter it is ready for use.

Example 3

Description of Tests

The powder and liquid described above were tested together in the below tests using a powder to liquid (P:L) ratio of 3.5:1. The material is either mixed by hand using a spatula by bringing the required amount of powder and liquid on to a mixing pad and mixing them thoroughly for 35 seconds, or by means of a capsule system. In the later case the powder and liquid have been pre-filled, in correct amounts to generate the required P:L ratio. Several different designs of such systems exist and anyone of these may be used. The capsule is first activated by bringing the powder and liquid together. The capsule is then transferred to a capsule mixing machine and mixed for a sufficient period of time. Using a 3M/ESPE Rotomix the time should be approximately 10 s with a 5 s centrifuge stage in the end. After mixing the ready material is dispensed using a therefore suited tool, into any desired sample mould or container. There is no significant difference in properties depending on whether the material is mixed by hand, or using a capsule system.

The tests performed on the material are the tests shown in table 2 and the results thereof are also provided in the table.

TABLE 2

| Test | ISO Classification | Outcome |
| --- | --- | --- |
| Cytotoxicity | ISO10993-5 | Non-cytotoxic within 15 min |
| Sensitization | ISO10993-10 | No sensitizing potential obtained in Guinea Pig Maximization Test |
| Irritation/Intra-cutaneous reactivity | ISO10993-10 | No discrepancies in irritation or delayed hypersensitivity after intracutaneous injections compared to placebo injections |
| Systemic toxicity | ISO10993-11 | Performed with both polar and nonpolar extracts from cured material; no signs of acute systemic toxicity |
| Sub-acute, sub-chronic and chronic toxicity | ISO10993-11 | No sub-acute, sub-chronic or chronic toxicity observed in two rabbit studies |
| Genotoxicity | ISO10993-3 | No bacterial toxicity, mutagenecity or clastogenic effect in mice nor in-vitro |
| Implantation | ISO10993-6 | Minimal inflammatory reactions in 6 week rabbit femur study; Granulomatous inflammation in the cavity, pigmented macrophages and new bone formation with deposits of aluminum observed at 6 and 12 month examination. |
| Acid erosion | ISO 9917: 2003 part 1 | In the test no erosion was able to be detected |
| Radio Opacity | ISO 9917: 2003 part 2 | 2.5 mm (Al-reference 2 mm) |
| Haemocompatibility | ISO10993-4 | The material neither induces haemolysis nor blood clotting |
| Biodegradation | ISO10993-9 | The material is an in vivo stable biomaterial |
| Compressive strength | ISO 9917: 2003 part 1 | Well above standard |
| Flexural strength | No ISO applicable, 4-point bending used | 40 MPa |

The results show that by producing an injectable paste according to the above description with a P:L ratio of 3.5:1 the above tests according to ISO standard tests are fulfilled.

The pH was measured during the first hour in phosphate buffer system, and the pH value showed a decrease according to Table 3.

TABLE 3

| Time after paste preparation in minutes | pH |
| --- | --- |
| 0 | 11.5 |
| 5 | 10.5 |
| 10 | 10.0 |
| 20 | 9.5 |
| 60 | 8.5 |

Regarding the bioactivity, it has been shown by means of energy dispersive spectroscopy (EDS), scanning electron microscopy (SEM), transmission electron microscopy (TEM), grazing incidence X-ray diffraction (GI-XRD) that a layer of crystallised hydroxyl apatite is formed on the surface of the material when submerged in phosphate buffered saline (PBS) for a period of 7 days.

The invention claimed is:

1. A method of treating or preventing periimplantitis in a subject in need of a dental implant, comprising the following steps:
    providing a powder comprising a powdered cement comprising calcium aluminate, and optionally a calcium silicate phase $C_3S$;
    providing an aqueous hydration liquid containing LiCl;
    mixing the powdered cement and hydration liquid so as to form a paste;
    wherein the calcium aluminate consists of particles of the phases CA and/or $C_{12}A_7$, and optionally $C_3A$, and wherein the combined amounts of any $C_3A$ and $C_3S$ present do not exceed 10% by weight of the powdered cement, and
    wherein the powdered cement exhibit a mean particle size within the interval of 2-7 μm, and the powder to liquid ratio is within the range of 2.0:1 to 5.0:1; and
    applying the paste to a surface of a dental implant, wherein said surface is to be in contact with bone tissue, in order to treat or prevent periimplantitis in said subject.

2. The method of claim 1 further comprising the step of treating said implant surface with an aqueous solution of $C_3S$, CaO and/or $C_3A$ before applying the paste to said surface.

3. The method of claim 1, further comprising the step of implanting said implant into bone tissue.

4. The method of claim 1, wherein the pH interval during hydration is controlled to be within the interval of 8.5-12.5, the temperature is controlled to be within the interval of 37-60° C., and the hydration time is controlled to be within the range of 5-60 minutes.

5. The method of claim 1, wherein the total volume of paste applied to the implant is less than 0.8 $cm^3$.

6. The method of claim 5, wherein the total volume of paste applied to the implant is less than 0.5 $cm^3$.

7. The method of claim 1, wherein said powdered cement further comprises inert filler particles.

8. The method of claim 1, wherein said implant is located in said subject.

* * * * *